United States Patent [19]
Takikawa

[11] Patent Number: 5,727,454
[45] Date of Patent: Mar. 17, 1998

[54] DEVICE FOR MARKING AN ELONGATE MATERIAL

[75] Inventor: Katsunobu Takikawa, Hachioji, Japan

[73] Assignee: Takikawa Engineering Co., Ltd., Japan

[21] Appl. No.: 723,265

[22] Filed: Sep. 30, 1996

[30] Foreign Application Priority Data

Nov. 1, 1995 [JP] Japan ................................ 7-308247
Aug. 21, 1996 [JP] Japan ................................ 8-219746

[51] Int. Cl.⁶ ................................................. B65B 13/02
[52] U.S. Cl. ................................. 100/4; 100/9; 53/582
[58] Field of Search ........................ 156/84, 160, 350,
156/229, 434, 443, 494, 510, 583.1; 53/399,
582; 100/9, 17, 18, 19 R, 33 PB, 4; 198/736,
747, 749

[56] References Cited

U.S. PATENT DOCUMENTS 2,514,038  7/1950  Doolittle ........................ 100/9
3,964,380  6/1976  Meyer et al. .................... 100/9
4,312,173  1/1982  Killermann ...................... 100/9

FOREIGN PATENT DOCUMENTS 56-162044  12/1981  Japan .
56-162045  12/1981  Japan .
62-261957  11/1987  Japan .
62-278444  12/1987  Japan .
64-87169    3/1989  Japan .

Primary Examiner—Richard Crispino
Attorney, Agent, or Firm—Zarley, McKee, Thomte, Voorhees, & Sease

[57] ABSTRACT

A device for marking an elongate material moving along a longitudinal path includes a support with an opening therein for the elongate material to pass through, a holding/releasing mechanism on the support for expanding and releasing an elastic ring onto the elongate material, the holding/releasing mechanism including drive means for releasing the ring, and a defect detection sensor disposed upstream of the holding/releasing mechanism for activating the drive means to release the elastic ring onto the elongated material when a defect is detected therein.

2 Claims, 7 Drawing Sheets

1
DEVICE FOR MARKING AN ELONGATE MATERIAL

BACKGROUND OF THE INVENTION

The present invention relates to a method of marking a required position, such as the location of a defect, on an elongate material such as an electric wire, a pipe and a hose, and a device for carrying out the method.

While electric wires continuously manufactured are wound around a winding drum in a factory, they are inspected by a defect detecting sensor of a detecting device such as an outer diameter laser measuring instrument, an ultrasonic detecting device and eddy current to inspect whether defects are made. If a defect should be found, a mark is made in the vicinity thereof, and thereafter, the defect is cut or modified based on the marking.

As a conventional method of marking elongate material such as electric wire which runs in a longitudinal direction, there is a method of spraying paint, such as inks, to the elongate material, or attaching sealing wax thereto.

However, it is troublesome to remove adhered paintings if such defects are not actually found by reexamination or if the defects are removed by simple modification. Also, with variation of feed rate of elongate material, thickness of paintings is varied, thereby making it difficult to regulate spray coverage. Furthermore, it is difficult to spray the whole circumference of the elongate material. If only one side is sprayed, it will be difficult to find the mark, and one is liable to miss it.

In the foregoing method of attaching seals, depending on the surface condition of the elongate material, attachment is impossible. If anything easily removable is used, the marking is removed during transportation or it is difficult to attach seal to the whole circumference of the elongate material, just as with spray painting.

SUMMARY OF THE INVENTION

In view of the disadvantages in the prior art, it is an object to provide a method of marking the circumference of an elongate material easily regardless of feed rate of the elongate material and removing the marking easily after completion.

To achieve the object, according to one aspect of the present invention, there is provided a method of marking an elongate material which runs in a longitudinal direction, the method comprising the steps of:

providing a ring of elastic material in which the circumference is smaller in a free state than that of the elongate material;

expanding the ring of elastic material so that the circumference thereof is larger than that of the elongate material to surround a running path of the elongate material; and releasing and thereby allowing the ring of elastic material when a position to be marked in the elongate material comes to a position corresponding to the ring of elastic material to wind the ring of elastic material around the circumference of the elongate material.

According to another aspect of the invention, there is provided a device for marking an elongate material, the device comprising:

a support which has an opening through which the elongate material extends in a longitudinal direction; and an elastic material holding/releasing mechanism mounted on the support to expand an elastic material ring in which the circumference is smaller in a free state than that of the elongate material ring to hold the elastic material ring around the elongate material, drive means releasing holding condition of the elastic material and shrinking the elastic material ring by restoring force to wind it around the elongate material.

Regardless of feed rate of the elongate material, marking can be made around the whole circumference of the elongate material, and after use, by cutting off the elastic material ring, marking can be easily removed.

BRIEF DESCRIPTION OF THE DRAWINGS

The features and advantages of the present invention will become more apparent from the following description with respect to the embodiment as shown in the appended drawings wherein.

DETAILED DESCRIPTION OF THE PREFERRED EMBODIMENT

Figure 1:
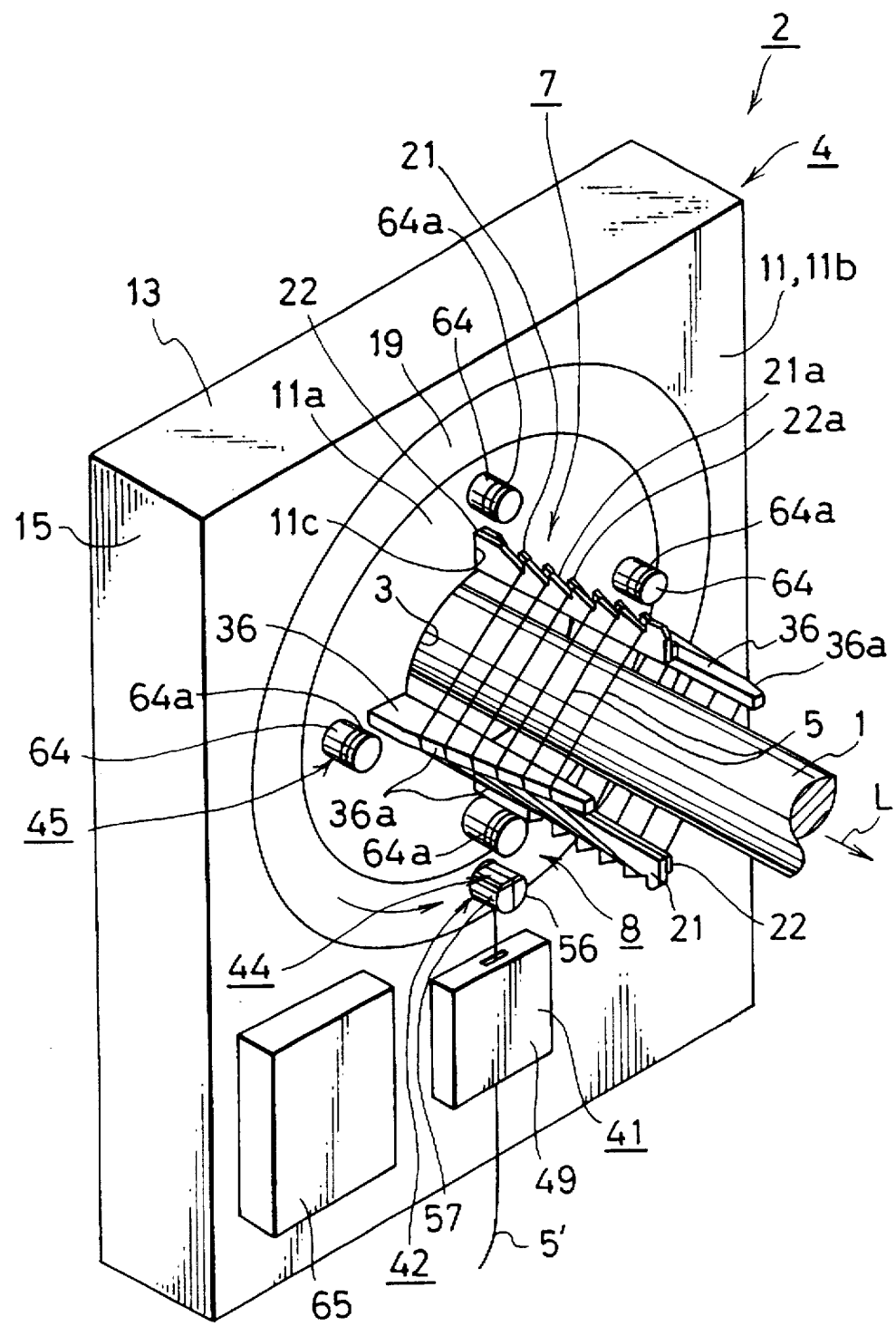
FIG. 1 is a perspective view of one embodiment of a device according to the present invention.

In FIG. 1, 1 denotes an elongate material which runs in a longitudinal direction, and a relatively large diameter telecommunication cable which is continuously manufactured. 2 denotes a marking device disposed in a running path "L" for the elongate material from a manufacturing machine to a rolling apparatus (not shown). The marking device 2 comprises a support 4 which has an opening 3 through which the elongate material goes; an elastic material holding mechanism 7 on the support 4 for expanding a an elastic material ring 5 in which the peripheral length is smaller in a free state than the outer circumference of the elongate material, thereby surrounding the annular elastic material 5, while drive means 6 operates to release supporting condition of the elastic material ring 5, thereby shrinking the annular elastic material 5 by its restoring force to wind it around the outer circumference of the elongate material 1; and an elastic material preparing mechanism 8 for preparing the elastic material ring 5 from a linear elastic material 5' at or adjacent to the position where the annular elastic material 5 is held and released by the elastic material holding/releasing mechanism 7.

The elements in the device according to the present invention will be described in detail as follows.

SUPPORT 4

Figure 2:
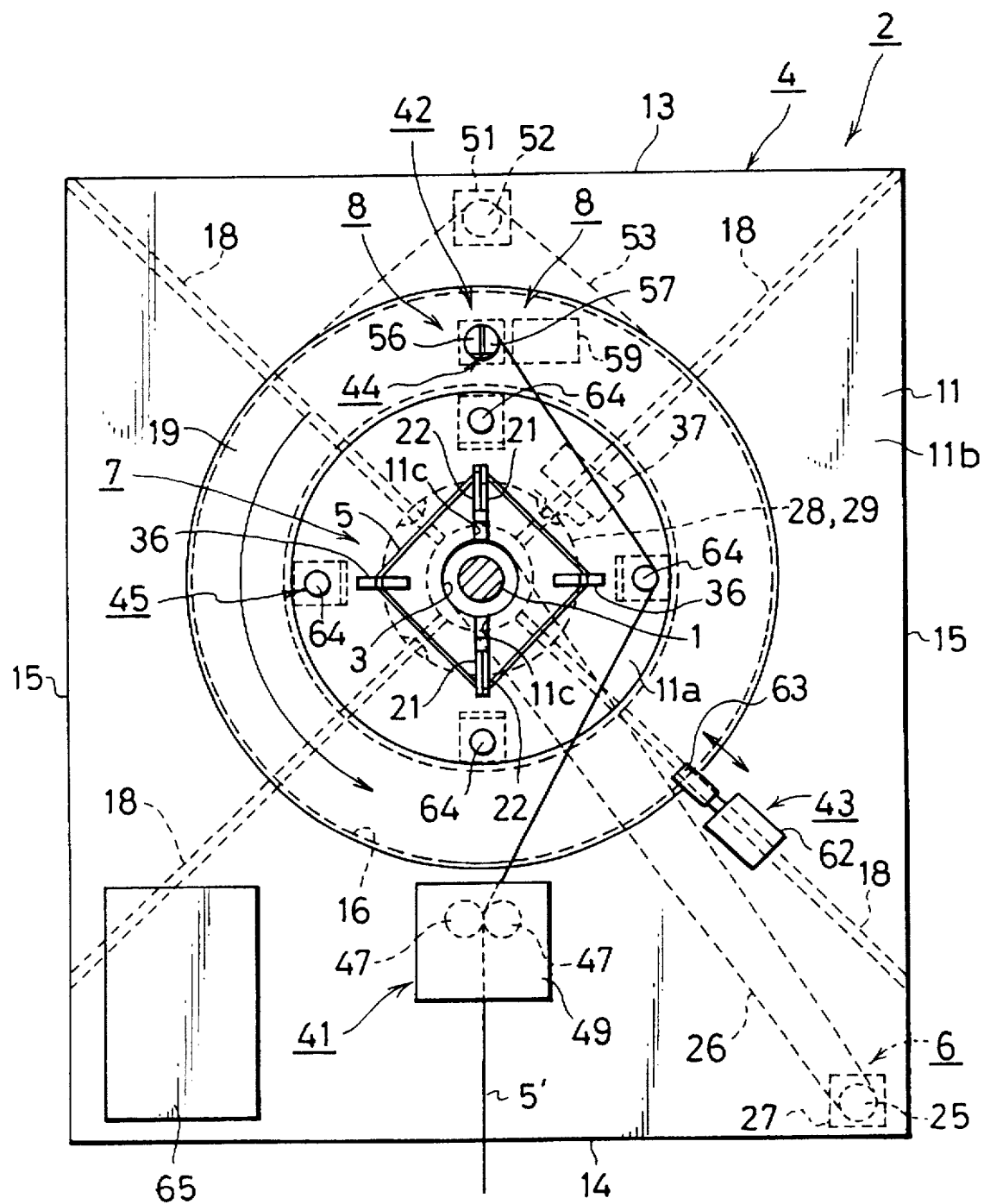
FIG. 2 is a front elevational view of the same when gripping fingers are moved to the upper position.
Figure 3:
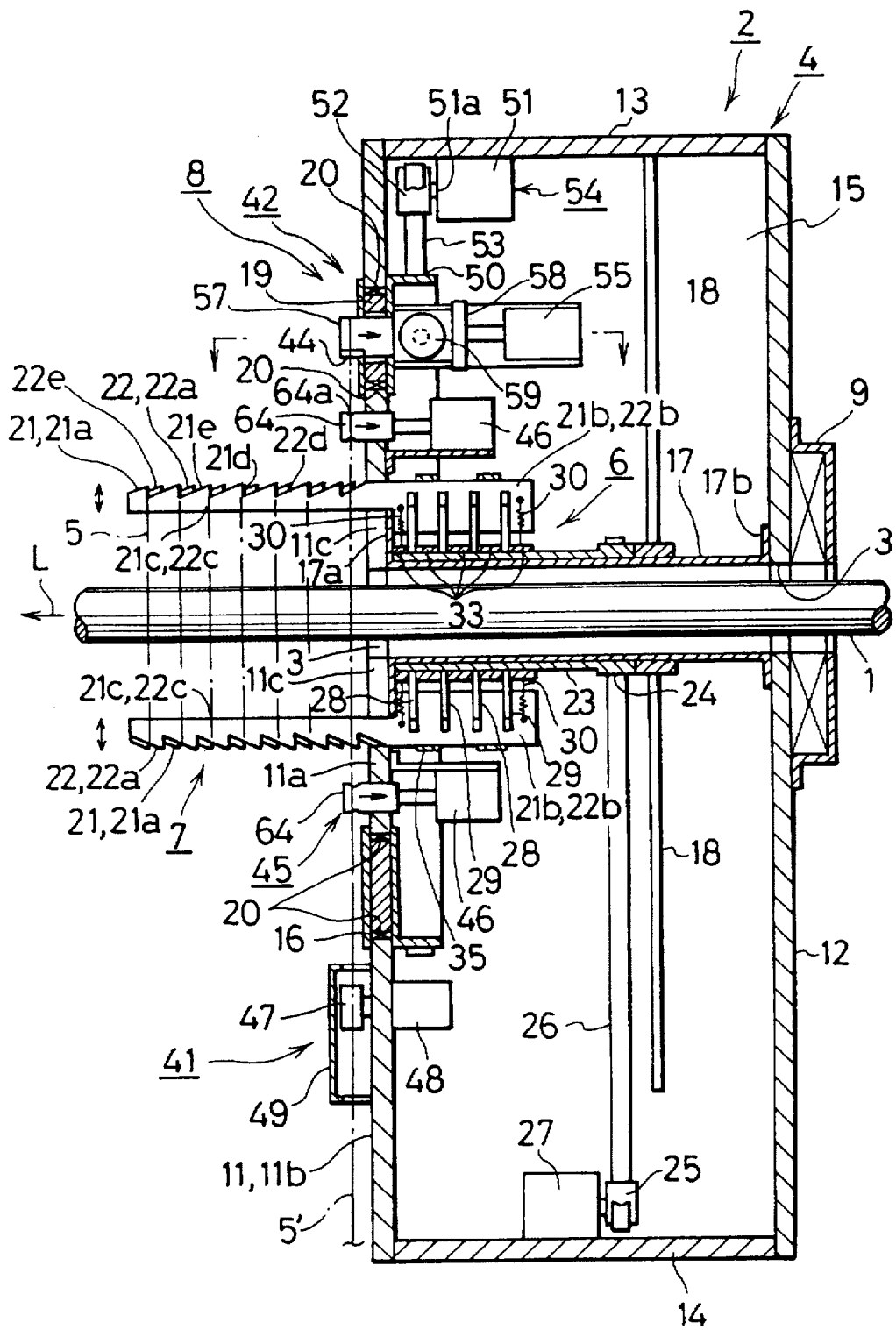
FIG. 3 is a central longitudinal sectional side view thereof.

In FIGS. 1 to 3, especially in FIG. 3, the support 4 comprises a pair of front and rear plates 11 and 12 having the opening 3 through which the elongate material 1 goes in the middle; an upper plate 13; a bottom plate 14 and side plates 15. (Forwarding direction of the material 1 is deemed "front".)

The front plate 11 comprises a first front plate 11a which comprises a disc concentric with the opening 3; and a second front plate 11b having a guide bore 16 having a larger diameter than the outer diameter of the first front plate 11a to surround the outer circumference of the first front plate 11a to surround the outer circumference of the first front plate 11a to surround the outer circumference of the first front plate 11a with a predetermined space. The first front plate 11a is fixed to an outward flange 17a provided at the front end of a guide tube 17 in the opening 3 of the front and rear plates 11 and 12. The outward flange 17b of the guide tube 17 is fixed to the rear plate 12, and the intermediate portion of the guide tube 17 is supported by a plurality of support rods 18 radially disposed in the support 4.

In an annular space between the first and second front plates 11a and 11b, a rotary ring 18 of the elastic material preparing mechanism 8 is rotatably provided on a bearing 20.

On the rear surface of the rear plate 12 of the support 4, there is provided a defect detecting sensor 9 to surround the running path "L" for the elongate material 1, the defect detecting sensor comprising a known outer diameter laser measuring device for measuring the outer diameter of the elongate material at any time to make output signals for operating the drive means 6 of the elastic material holding/releasing mechanism 7 when a measured value exceeds a predetermined range.

Elastic Material Holding/Releasing Mechanism 7

As shown in FIGS. 1 to 4, the elastic material holding/releasing mechanism 7 comprises two pairs of holding plates 21, 22 which are mounted to the support 4 around the opening 3 to be radially movable and have serrated guide edges 21a, 22a respectively; and drive means 6 for reciprocating at least on of the holding plate 21, 22 with respect to the other radially.

The holding plates 21, 22 comprise rectangular base portions 21b, 21b in the support 4; and arms 21c, 22c which project forward of the support 4 through a slit 11c provided radially of the opening 3 on the first front plate 11a. On the outer side peripheries of the arms 21c, 22c, there are provided serrated guide edges 21a, 22a which comprise vertical edges 21d, 22d perpendicular to the running path "L" of the elongate material 1; and oblique edges 21e, 22e inclined from the upper end of the vertical edges 21d, 22d forwardly and downwardly toward the elongate material 1. The guide edges 21a, 22a are longitudinally staggered about one-half a pitch apart.

The drive means 6 comprises a rotary tube 23 which rotatably surrounds a front half of the guide tube 17; a motor 27 in the support 4 for rotating the rotary tube 23 via pulleys 24, 25 and a belt 26; four axially spaced cam plates 28, 29 which are engaged on the outer circumference of the rotary tube 23 and have grooves 28a, 29a (or projections) at different lateral positions about 180 degrees apart; and a tension spring 30 for actuating the holding plates 21, 22 towards the center. The four cam plates 28, 29 which have two grooves 28a, 29a spaced apart from each other about 180 degrees are arranged alternatingly to allow the grooves of one of the cam plates to have angular positions different from those of adjacent cam plate by about 90 degrees.

Figure 4:
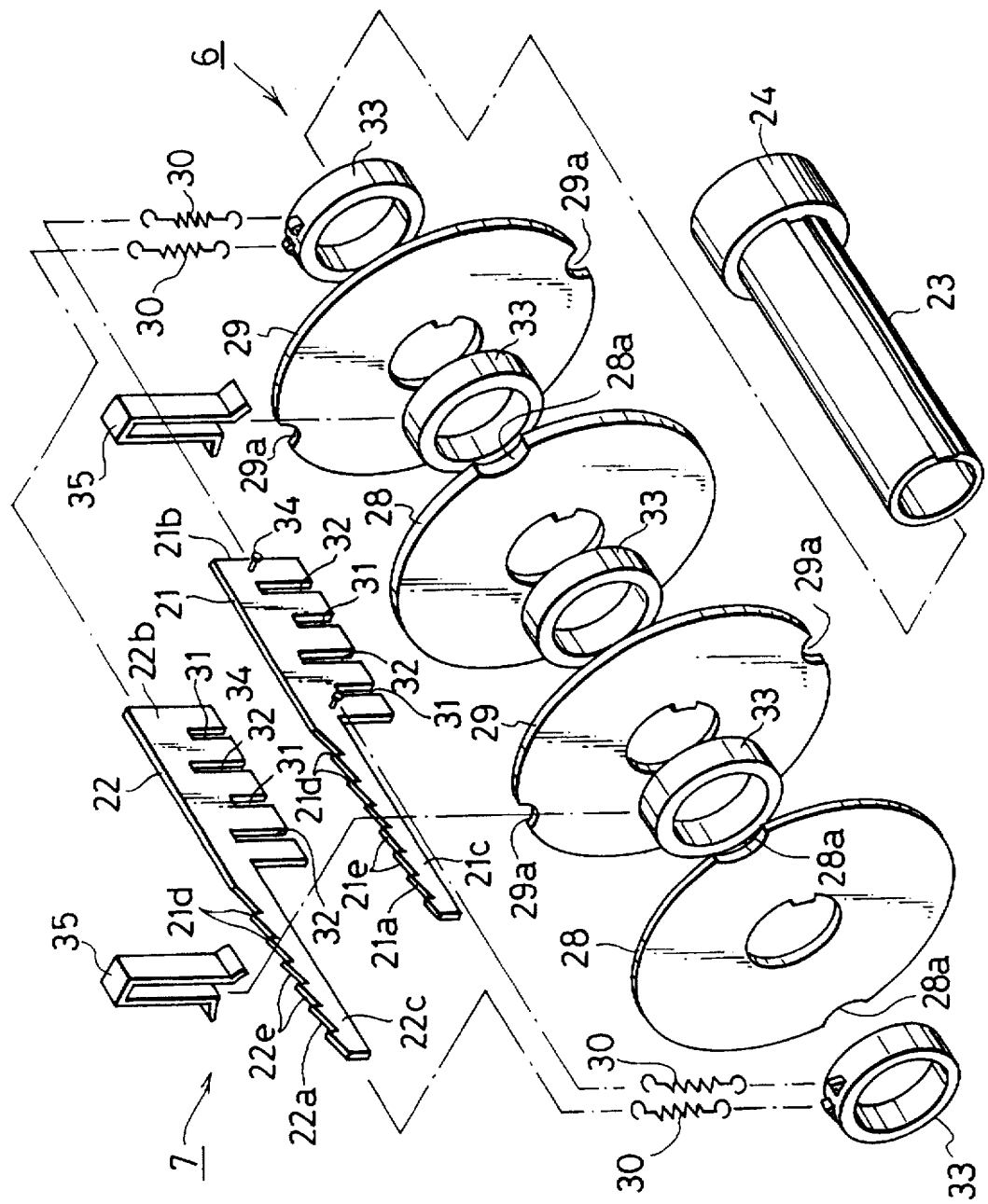
FIG. 4 is an exploded perspective view of the main portion thereof.

The base portions 21b, 22b of the holding plates 21, 22 have grooves 31, 32 having different depths of cut and are engaged with the cam plates 28, 29. As shown in FIG. 4, there are smaller depths of cut in the first and third grooves 31 of the holding plate 21 and in the second and fourth grooves 31 of the other holding plate 22, while there are larger depths of cut in the second and fourth grooves 32 of the holding plate 21 and in the first and third grooves 32 of the other holding plate.

Thus, when the grooves 28a, 28a of the cam plate 28 are positioned at the top and bottom and the grooves 29a, 29a of the cam plate 29 are positioned at the right and left, the holding plate 21 is movable by the tension spring 30 towards the center by an amount corresponding to the depth of the groove 28a. On the contrary, when the grooves 28a, 28a of the cam plate 28 are positioned at the right and left and the grooves 28a, 28a of the cam plate 28 re positioned at the top and bottom, the holding plate 22 is movable by the tension spring towards the center by an amount corresponding to the depth of the groove 28a by the tension spring 30. With rotation of the rotary tube 2, two conditions as above are alternately repeated, so that the two holding plates 21, 22 in each pair are alternately moved outwardly and inwardly in a radial direction.

As shown in FIGS. 3 and 4, the tension springs 30 are mounted at one end to the first and fifth of five spacer rings 33 which are slidably mounted on the rotary tube 23, and mounted at the other end to pins 34 projected on the side surfaces of the holding plates 21, 22, thereby yieldingly urging the holding plates 21, 22 towards the center at all times.

On the outer circumferential surface of the second and fourth spacer rings 33, 33, guide frames 35 which surround the two holding plates 21, 22 to guide radial movement thereof are fixed.

As shown in FIG. 1, on the first front plate 11a of support 4, a plurality of auxiliary guide plates 36 (two in this embodiment) which have oblique guide edges 36a tapered towards the forward direction of the elongate material 1 are provided between the holding plates 21, 22 in a cirumferential direction around the opening 3.

As shown in FIG. 1, a plurality of stretched elastic material rings 5 made of rubber are wound around the upper and lower holding plates 21, 22, and the right and left auxiliary guide plates 36 on each of the serrated guide edges 21a, 22a of the holding plates 21, 22. By the drive means 6, the two holding plates 21, 22 in each pair are alternately moved in a radial direction, so that the elastic material ring 5 is alternately transferred to the oblique edges 21e, 22e, and goes forwards by half a pitch along the oblique edges 21e, 22e. The elastic material ring 5 winds around the elongate material 1 as it feeds forward from the end of the holding plates 21, 22 and the auxiliary guide plate 36 is shrunk by restoring force.

The numeral 37 FIG. 2 denotes a limit switch prodded at the rear surface of the first front plate 11a, the limit switch 37 being operated when the groove 28a of the forwardmost cam plate 28.

With respect to control of the drive means 6, the motor 27 usually stops when the groove 28a of the forwardmost cam plate 28 is adjacent the limit switch 37 while the defect detecting sensor 9 operates or after a predetermined delay time, the motor 27 rotates the rotary tube 23. The rotary tube 23 rotates one half turn, and the next groove 28a of the forwardmost cam plate 28 is adjacent the limit switch 37, which stops the motor 27. During the time, the elastic material ring 5 advances forward by one pitch, and the elastic material ring 5 at the front end is wound around the elongate material 1.

The delay from operation of the defect detection sensor 9 to operation of the motor 27 is predetermined based on the feed rate of the elongate material land the distance from the defect detecting sensor 9 to the position where the front end elastic material ring 5 is released, or is automatically determined based on feed rate of the elongate material 1.

Elastic Material Preparing Mechanism 8

As shown in FIGS. 1 to 6, the elastic material preparing mechanism 8 comprises linear elastic material feed means 41 for feeding the linear elastic material 5' along the side of the support 4; grasping circulation means 42 for grasping the end of the linear elastic material 5' fed from the linear elastic material means 41 to circulate around the elastic material holding/releasing mechanism 7; fixing means 43 (in FIG. 2) for fixing the end of the linear elastic material 5' grasped and circulated by the grasping circulation means 42 to the other portion of the linear elastic material 5' grasped and circulated by the grasping circulation means 42 to the other portion of the linear elastic material 5' to form a ring portion 5" (FIG. 7); cutting means 44 for cutting linear elastic material 5' in order to continuously form the ring portion 5"; a winding frame 45 comprising a plurality of guide pins 64 retractably provided on the support 4 to surround the elastic material holding/releasing mechanism 7; and retraction drive means 46 for retracting the winding frame 45 with respect to the support 4.

Each of the structural elements in the mechanism 8 will be described in detail as follows.

The linear elastic material 5' and the elastic material ring 5 may be preferably made of synthetic rubber which contains 20% by weight of styrene and 70% by weight of butadiene as main ingredients.

The linear elastic material feed means 41 comprises a pair of pinch rollers 47, 47 on the front surface of the second front plate 11b; a motor 48 on the rear surface of the second front plate 11b for rotating one of the pinch rollers 47, 47, the linear elastic material 5' being put between the pinch rollers 47, 47 and fed to the running path "L" of the elongate material 1.

The grasping circulation means 42 comprises rotary means 54 in which a flat belt (or timing belt) 53 is wound between a larger diameter pulley 50 fixed on the rear surface of the rotary ring 19 and a pulley 52 fixed to a rotary shaft 51a of a motor 51 in the support 4 so that the rotary ring 19 is rotated by the motor 51.

Figure 5:
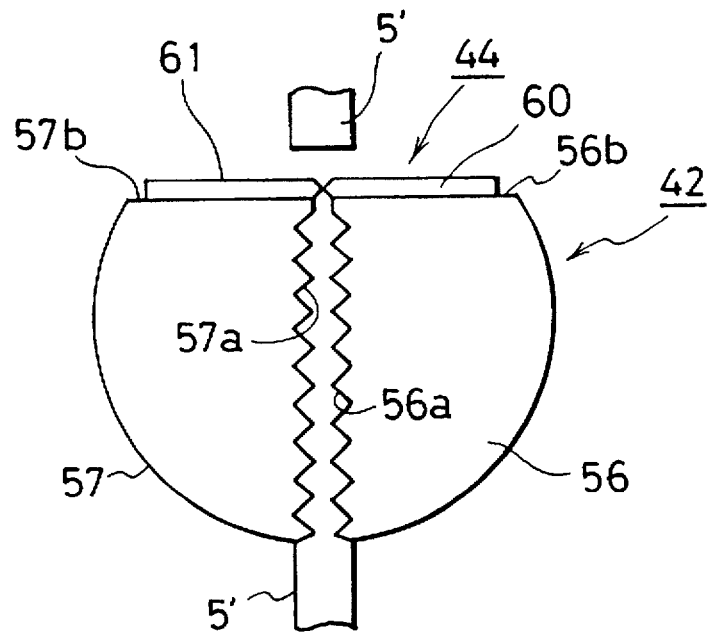
FIG. 5 is an enlarged front elevational view of the gripping finger.
Figure 6:
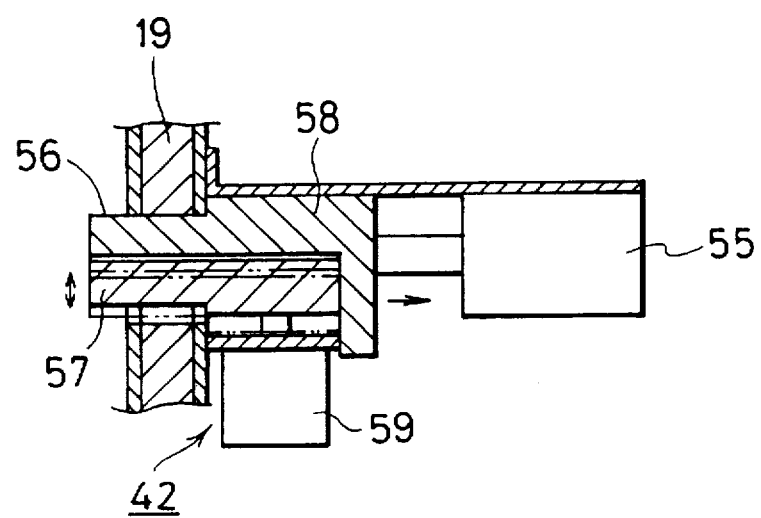
FIG. 6 is an enlarged sectional view taken along the line VI—VI in FIG. 3.

As shown in FIGS. 3, 5 and 6, the grasping circulation means 42 comprises a grasping body 58 in which a pair of grasping fingers 56, 57 are retractable from the front surface of the rotary ring 19 by retraction drive means 55 which comprises a linear solenoid on the rear surface of the rotary ring 19; and opening/closing means 59, which comprises a linear solenoid for opening and closing the grasping finger 57 with respect to the grasping finger 56, integrally formed with the grasping body 58.

As shown in FIG. 5, the grasping fingers 56, 57b have semicircular front surfaces, and there is a serration or wave on the opposing grasping surfaces 56a, 57a. On the flat surfaces 56b, 57b at the end of the grasping fingers 56, 57 near the running path "L" of the elongate material 1, there is cutting means 44 which comprises a pair of cutter blades 60, 61 for cutting the linear elastic material 5' between the grasping surfaces 56a, 57a when the grasping fingers 56, 57 are closed.

As shown in FIG. 2, the fixing means 43 comprises a welding heater 63 which is extendible from a retracted position to an extended position towards the running path "L" by moving means 62 which comprises a linear solenoid at the lower right portion of the front surface of the second front plate 12b. In the extended position, the welding heater 63 contacts the rotating grasping fingers 56, 57.

The winding frame 45 comprises four guide pins 64 retractably provided on four points which have an equal distance from the running path "L" on the front surface of the first front plate 12a, the four guide pins 64 being retracted by retractable drive means 46 (FIG. 3) which comprises a linear solenoid on the rear surface of the first front plate 12a. On the outer circumference of the end of each of the guide pins 64, there is formed an annular groove 64a to prevent the linear elastic material 5' wound thereon from disengaging as shown in FIG. 1.

The numeral 65 denotes means on the front surface of the second front plate 11b, by which each of the drive means is automatically operated based on a predetermined program, as follows.

A method of the present invention will be described with function of the above apparatus.

Before operation, the maximum number of elastic material rings 5 which can be reserved in the elastic material holding/releasing mechanism 7 were prepared by the ring elastic material preparing mechanism 8 and attached to the elastic material holding/releasing mechanism 7, providing a distance of one pitch between the rings 5.

Figure 7:
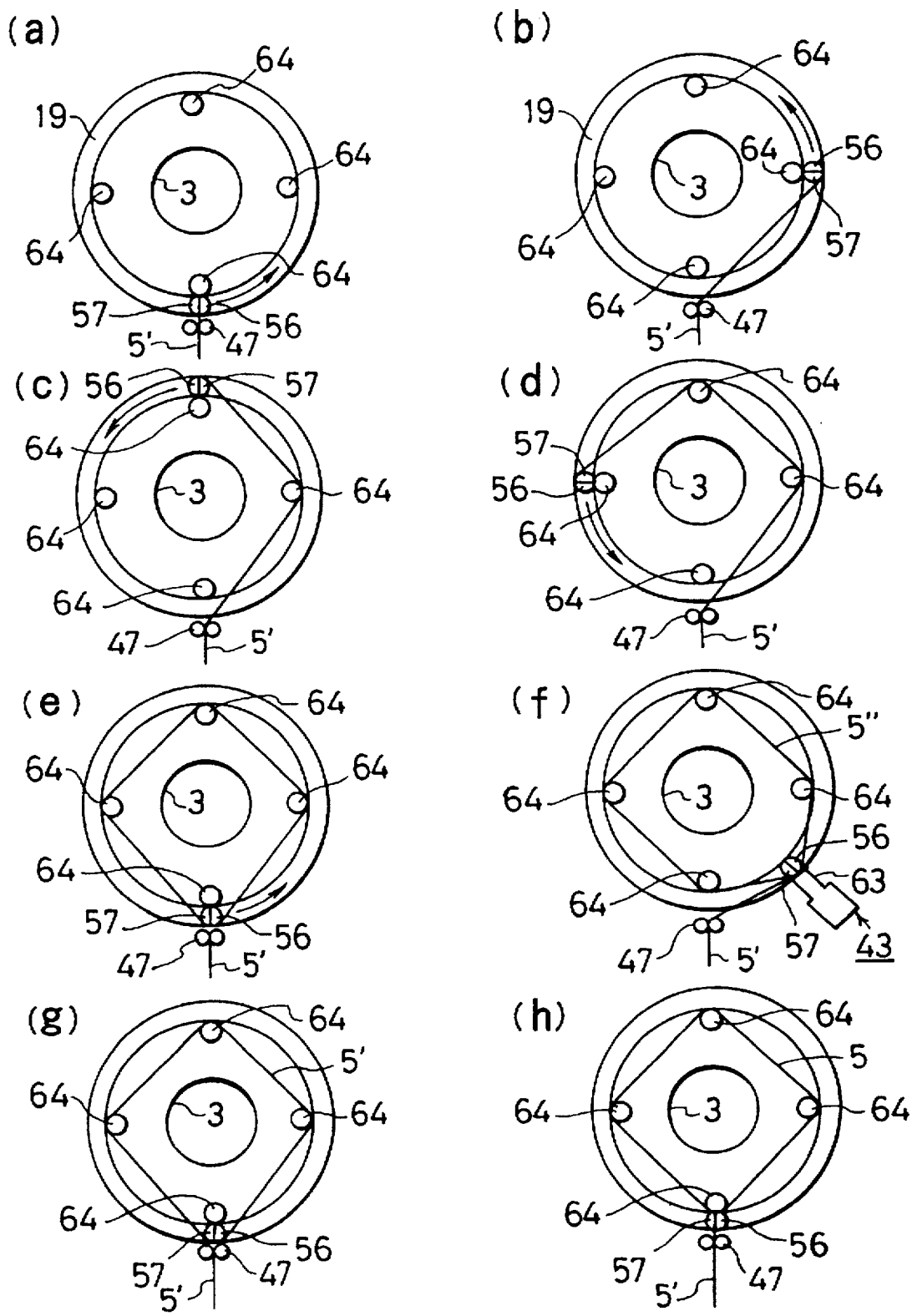
FIG. 7 is a compilation of views 7(a)–7(h) which illustrate the operation of a elastic material ring preparing mechanism.

The preparation of one elastic material ring 5 is illustrated in FIG. 7. The motor 48 of the linear elastic material feed means 41 is operated, so that the linear elastic material 5' is fed by the pinch rollers 47, 47. When the end of the material 5' is put between the grasping fingers 56, 57, it is cut by the cutter blades 60, 61 (see FIG. 5) in FIG. 7(a). Then, the motor 51 is operated, and the rotary ring 19 is rotated in the direction of the arrow in FIG. 7(a) by a total of 405 degrees. FIGS. 7(b) to 7(f) show the rotary ring 19 as it is rotated by 90, 180, 270, 360 and 405 degrees respectively. During the rotation, the feed rate of the linear elastic material 5' by the pinch roller 47 is lower than that of the grasping fingers 56, 57, so that the linear elastic material between the grasping fingers 56, 57 and the pinch rollers 47, 47 are wound around the four guide pins 64 while the material is stretched.

When the rotary ring 19 is rotated between 360 and 405 degrees, the second circuit linear elastic material 5' is overlapped on the end of the first circuit linear elastic material 5' outside the grasping finger 56. The rotary ring 19 is rotated by 405 degrees, and when the rotation is stopped, the moving means 62 of the fixing means 43 is operated, and the welding heater 63 is pressed against the outside of the grasping fingers 56, 57. Then, the welding heater 63 is electrically energized, so that the overlapped portion of the linear elastic material 5' as shown in FIG. 7(f). At the same time the rotation of the rotary ring 19 is stopped, feeding of the linear elastic material 5' by the pinch rollers 47, 47 is stopped.

Then, the motor 51 is reversed, and the rotary ring 19 is moved by 45 degrees in a clockwise direction. See FIGS. 7(g) and 7(h). After the motor 51 is stopped, the opening/closing means 59 is operated in an opening direction to open the grasping fingers 56, 57. Thereafter, the retraction drive means 55 is operated in a retracted direction, and the grasping fingers 56, 57 are retracted rearwards on the front plate of the support 4. Thus, the ring portion 5" of the linear elastic material 5' wound around the outside of the grasping fingers 56, 57 is disengaged from the grasping fingers 56, 57, and wound around the lowest guide pin 64 by self-shrinking force.

Thereafter, while the grasping fingers 56, 57 are opened, the retraction drive means 55 is operated in an extending direction, and the grasping fingers 56, 57 are moved forwards to the original position, so that a portion continuous to the ring portion 5" of the linear elastic material 5' is put between them. In this situation, the opening/closing means 59 is operated in a closing direction, and the grasping fingers 56, 57 are closed, so that the above portion of the linear elastic material 5' is held, and the ring portion 5" is cut off from a portion continuous thereto by the cutter blades 60, 61 to form a single elastic material ring 5.

Then, the retraction drive means 46 is operated in a retracting direction, and the four guide pins 64 are retracted rearwardly from the front surface of the support 4. The finished elastic material ring 5 is shrunk by self-shrinking force and wound around two pairs of holding plates 21, 22 and the two auxiliary guide plates 36 of the elastic material holding/releasing mechanism 7. At the same time or thereafter, the rotary ring 19 is rotated as above, and thereafter, by repeating the above operation, the elastic material rings 5 are formed one by one.

First the finished elastic material ring 5 is wound around a portion of arms 21c, 22c of the guide edges 21, 22a in the holding plates 21, 22 near the support 4; moved forwards by the elastic material holding mechanism 7; released from the end of the arms 21c, 22c finally; and wound around the elongate material 1.

Figure 8:
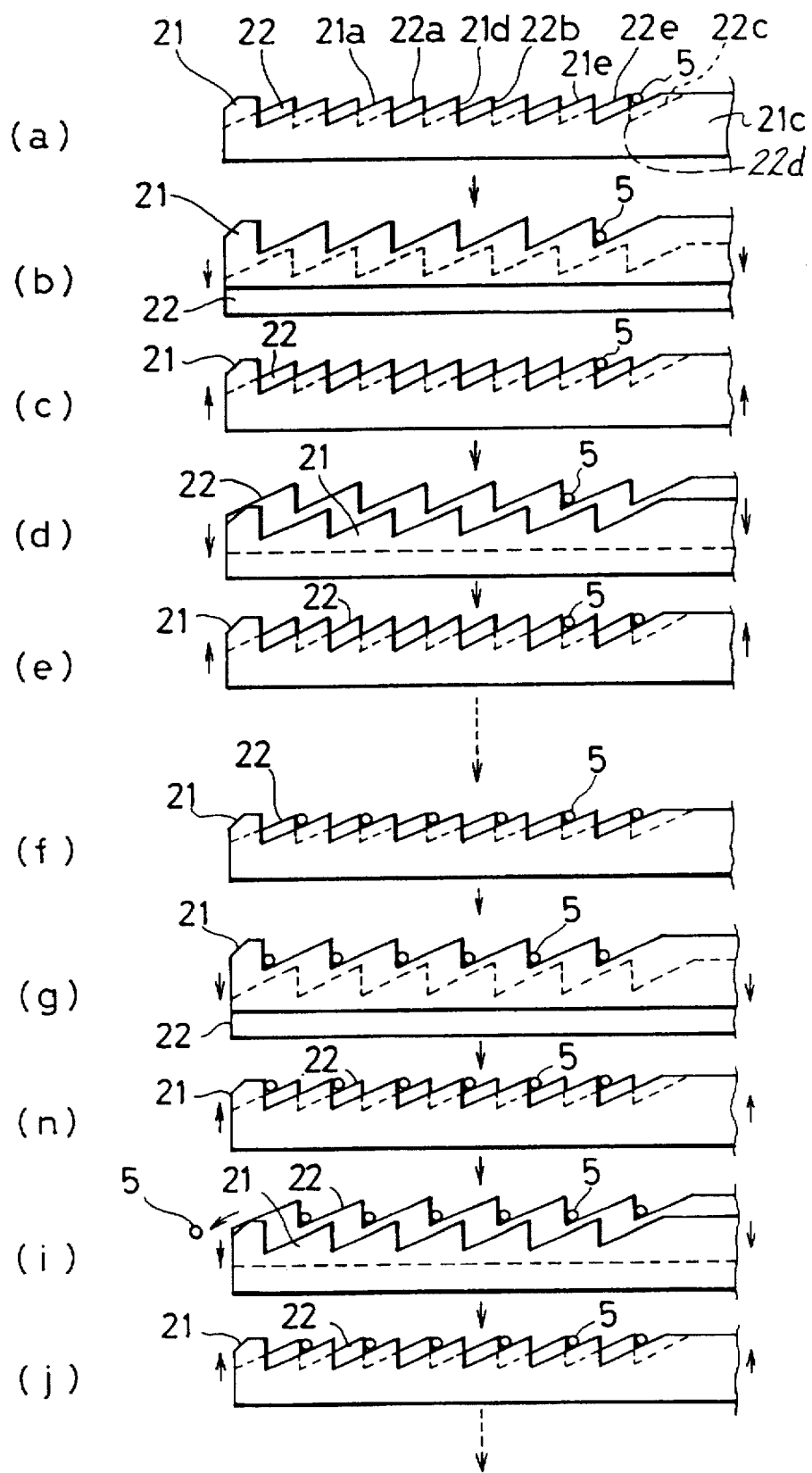
FIG. 8 is a compilation of views 8(a)–8(j) which illustrate the operation of an elastic material holding/releasing mechanism.

The operation of the elastic material holding/releasing mechanism 7 will be described with respect to FIG. 8.

As shown in FIG. 8(a), when the guide edges 21a, 22a of the holding plates 21, 22 have roughly equal heights, the first elastic material ring 5 is wound to engage with a root formed by an oblique edge 21e and a vertical edge 22d of the holding plate 22 near the support 4.

In this situation, the rotary tube 23 is rotated in a clockwise direction in FIG. 2 by the motor 27, so that the four cam plates 28, 29 in FIG. 4 are rotated together with the tube 23 in the same direction. When the four cam plates 28, 29 are rotated by 45 degrees, the grooves 29a of the cam plate 29 are positioned at the top and bottom, only the holding plate 22 is drawn toward the groove 29a by the tension spring 30. At this time, in the other holding plates 21, the bottom of the shallow groove 31 is slidably engaged on the outer circumferential edge of the cam plate 28 to prevent movement towards the center.

Owing to different movement between the holding plates 21 and 22, as shown in FIG. 8(b), the serrated guide edge 22a of the holding plate 22 moves down inward of the guide edge 21a, and the elastic material ring 5 goes forward along the first oblique edge 21e by advancing half a pitch. Once the groove 29a of the cam plate 29 passes through the holding plates 22, the holding plates 22 are displaced by the cam plate 29 and pushed out, so that the guide edge 22a is as high as the guide edge 21a of the holding plate 21, and the elastic material ring 5 is expanded to its original diameter.

When the rotary tube 23 is rotated by about 135 degrees from the beginning of the rotation, the grooves 28a of the cam plate 28 are positioned at the top and bottom, such that only the holding plates 21 are moved toward the center by an amount equal to the depth of the groove 28a, and the holding plates 22 are kept in such a position.

Owing to different movement of the holding plates 21 and 22, as shown in FIG. 8(d), the guide edge 21a of the holding plate 21 is moved down and pushed in a radial direction. As shown in FIG. 8(e), it is returned to the original position, and the elastic material ring 5 is expanded to the original diameter.

The rotary tube 23 is rotated by 180 degrees from the beginning of the rotation, and the groove 29a of the foremost cam plate 28 faces the limit switch 37 to actuate the limit switch 37, so that the motor 27 is stopped.

Owing to half a rotation of the rotary tube 23 and the cam plates 28, 29, the elastic material ring 5 advances forward by one pitch of the teeth of the serrated guide edges 21a, 22a, while its diameter is somewhat variable as above. Then, after the second ring-like elastic material 5 formed by the ring elastic material preparing mechanism 8 is the same position (FIG. 8(e)) as the first position (refer to FIG. 8(a)), the rotary tube 23 is again rotated by 180 degrees, the two elastic material rings 5 are moved forward by one pitch according to similar action described above.

Thus, every time the elastic material ring 5 is moved forward by one pitch, one new elastic material ring 5 is supplied. When the top ring 5 reaches to the top vertical edge 22b of the holding plate 22, the operation of the ring elastic material preparing mechanism 8 stops, and the preparation step is finished.

With respect to operation of the device, when the outer diameter of the elongate material 1 exceeds a predetermined value of the defect detecting sensor 9, the defect detecting sensor 9 is operated, thereby operating the motor 27 and rotating the rotary tube 23 by 180 degrees. In this situation, the elongate material preparing mechanism is operated. In an initiation step where the feed rate of the elongate material 1 reaches a predetermined rate, the outer diameter of the elongate material 1 is liable to vary greatly, so the defect detecting sensor 9 or motor 27 may not be operated.

After the feed rate of the elongate material 1 reaches a predetermined rate, it varies until the outer diameter of the elongate material 1 exceeds a predetermined value, so that the defect detecting sensor 9 is operated, thereby operating the motor 27 and rotating the rotary tube 23 by 180 degrees as above.

During the rotation of the rotary tube 23, the holding plates 21, 22 move one reciprocating motion at different times as shown in FIG. 8(f) to 8(j), similar to (a) to (e). The top elastic material ring 5 goes forward by half a pitch of the serrated teeth when FIG. 8(f) is shifted to (g), and it goes forwards by another half a pitch when (h) is shifted to (i), so that it is released from the end of the arms 21c, 22c of the holding plates 21, 22, shrunk by self-restoring force, and wound around the elongate material 1.

With this invention it takes the same amount of time for the ring 5 to be windingly advanced and released as it takes for the defective (oversized) portion of the elongate material 1 to move from the defect detecting sensor 9 to the point where the ring 5 is released. Thus, the ring 5 can be precisely placed directly on the defect.

When such accuracy is not required, the distance between the winding position and the defect detecting sensor 9 is suitably estimated, so that the elastic material ring 5 can be wound around a portion near the defect.

In the foregoing embodiments, the linear and ring elastic materials 5', 5 are made of synthetic rubber, but elastic material such as natural rubber and thermoplastic elastomer may be used.

It is contemplated that non-elastic material, such as heat-shrinkable material and shape memory alloy, can be wound around the whole outer circumference of the elongate material owing to temperature change, but it is necessary to provide heating means, which is troublesome to control and involves low reliability or utility. On the contrary, according to the present invention, it is not necessary to provide such heating means. It is possible to operate the present invention more readily, thereby providing high utility.

In the foregoing embodiments, both of the two holding plates 21, 22 are alternately moved to the center, but similar advantages may be achieved by fixing one of them on the support 4, the other being moved toward a center or in a radial direction, or by mounting to one end of the support 4 rotatably, the other being rotated in the radial direction.

Furthermore, the present invention may apply not only to a case where marking is applied to a defect of the elongate material, but also to a case where marking is applied to a fixed length of the elongate material by combining with a sensor for detecting feed rate of the elongate material so that the elongate material is cut at intervals based on the marking.

Modifications and changes may be carried out by person skilled in the art without departing from the scope of claims of the appended claims.

What is claimed is:

1. A device for marking an elongate material moving along a longitudinal path, comprising:

a support with an opening for the elongate material to pass through;

a holding/releasing mechanism mounted on said support to expand and release an elastic material ring to apply the ring around the elongate material, said holding/releasing mechanism comprising drive means for releasing the elastic material ring; and a defect detecting sensor disposed upstream of the holding/releasing mechanism and in the path of the elongate material the drive means of the holding/releasing mechanism being activated by the sensor to release the elastic material ring onto the elongate material when a defect in the elongate material is detected by the sensor.

2. The device as defined in claim 1 wherein the defect detecting sensor comprises an outer diameter measuring instrument for measuring an outer diameter of the elongate material and actuating the drive means of the holding/releasing mechanism when a measured value exceeds predetermined range.

* * * * *